United States Patent [19]

Urnovitz

[11] Patent Number: 5,447,837

[45] Date of Patent: Sep. 5, 1995

[54] MULTI-IMMUNOASSAY DIAGNOSTIC SYSTEM FOR ANTIGENS OR ANTIBODIES OR BOTH

[75] Inventor: Howard B. Urnovitz, San Francisco, Calif.

[73] Assignee: Calypte, Inc., Berkeley, Calif.

[21] Appl. No.: 307,361

[22] Filed: Feb. 6, 1989

Related U.S. Application Data

[63] Continuation-in-part of Ser. No. 81,874, Aug. 5, 1987, abandoned.

[30] Foreign Application Priority Data

Aug. 5, 1988 [CA] Canada .................................. 573926

[51] Int. Cl.⁶ .............................................. C12Q 1/70
[52] U.S. Cl. ................................ 435/5; 435/7.920; 435/7.930; 435/7.940; 435/7.950; 435/962; 435/973; 435/974; 436/518; 436/523; 436/524; 436/528; 436/531; 436/825
[58] Field of Search ............... 435/7, 805, 810, 7.9, 435/7.92, 7.95, 973, 974, 5, 962; 436/501, 514, 518, 523, 524, 528, 807, 531, 810, , 825, 820, 513; 422/55

[56] References Cited

U.S. PATENT DOCUMENTS

| | | | |
|---|---|---|---|
| Re. 31,006 | 8/1982 | Schuurs et al. | 435/7 |
| 3,888,629 | 6/1975 | Bagshawe | 23/230 |
| 4,094,647 | 6/1978 | Deutsch et al. | 23/253 |
| 4,125,372 | 11/1978 | Kawai et al. | 23/230 |
| 4,208,479 | 6/1980 | Zuk et al. | 435/7 |
| 4,235,601 | 11/1980 | Deutsch et al. | 23/230 |
| 4,278,653 | 7/1981 | Harris et al. | 424/1 |
| 4,294,817 | 10/1981 | Burgett et al. | 424/8 |
| 4,299,916 | 11/1981 | Litman et al. | 435/6 |
| 4,305,924 | 12/1981 | Piasio et al. | 424/1 |
| 4,361,537 | 11/1982 | Deutsch et al. | 422/56 |
| 4,366,242 | 12/1982 | Neumann et al. | 435/7 |
| 4,376,110 | 3/1982 | David et al. | 436/513 |
| 4,424,279 | 1/1984 | Bohn et al. | 436/534 |
| 4,458,020 | 7/1984 | Bohn et al. | 435/296 |
| 4,464,474 | 8/1984 | Goursaget | 436/513 |
| 4,496,654 | 1/1985 | Katz et al. | 435/7 |

(List continued on next page.)

FOREIGN PATENT DOCUMENTS

| | | | |
|---|---|---|---|
| 88/10741 | 7/1988 | Australia . | |
| 63810 | 11/1982 | European Pat. Off. | G01N 3/54 |
| 0093613 | 3/1983 | European Pat. Off. | G01N 33/54 |
| 0173295 | 5/1986 | European Pat. Off. | 435/973 |
| 0200381 | 5/1986 | European Pat. Off. | 435/7 |
| 0201716 | 7/1986 | European Pat. Off. | C12N 15/00 |

(List continued on next page.)

OTHER PUBLICATIONS

Bangs, Uniform Latex Particles, Seradyn Inc. 1984 p. 3.
Microparticle Immunoassay Techniques, 2nd ed. Seradyn, Inc. 1988 pp. 1–10.

(List continued on next page.)

*Primary Examiner*—Carol A. Spiegel

[57] ABSTRACT

The present invention provides a test strip for detecting, in a sample from a human subject, the presence of an antigenic substance which comprises a solid support, an antibody directed against the antigenic substance bound to a first discrete area on the solid support, an anti-human antibody bound to a second discrete area on the solid support as a positive control, and an antibody directed against an antigen which does not naturally occur in human subjects bound to a third discrete area on the solid support as a negative control. The present invention also provides a test strip for detecting, in a sample from a human subject, the presence of an antibody which comprises a solid support, an antigenic substance bound to a first discrete area on the solid support, an anti-human antibody bound to a second discrete area on the solid support as a positive control, and a negative control bound to a third discrete area on the solid support. The invention further provides a test strip for detecting the presence of an antibody and antigenic substance, which may additionally comprise an antibody-based reagent directed against the antigenic substance in an immune complex and native human antibody thereto. The invention also provides a method for detecting in a sample from a human subject the presence of an antigenic substance or antibody or both using the aforementioned test strips.

10 Claims, 2 Drawing Sheets

U.S. PATENT DOCUMENTS

| | | | |
|---|---|---|---|
| 4,533,629 | 8/1985 | Litman et al. | 435/805 X |
| 4,540,659 | 9/1985 | Litman et al. | 435/7 |
| 4,558,013 | 12/1985 | Marinkovich et al. | 436/513 |
| 4,567,149 | 1/1986 | Sell et al. | 436/513 |
| 4,623,461 | 11/1986 | Hossom et al. | 210/445 |
| 4,629,783 | 12/1986 | Cosand | 530/324 |
| 4,680,274 | 7/1987 | Sakai et al. | 436/825 X |
| 4,725,669 | 2/1988 | Essex | 530/322 |
| 4,737,456 | 4/1988 | Weng et al. | 436/825 X |
| 4,748,042 | 5/1988 | Linnecke et al. | 436/530 X |
| 4,784,941 | 11/1988 | Watanabe | 435/5 |
| 4,808,536 | 2/1989 | Chang et al. | 435/5 |
| 4,851,210 | 7/1989 | Hewett | 436/513 X |
| 4,865,966 | 9/1989 | Friedman-Kem et al. | 435/5 |
| 4,877,725 | 10/1989 | Neurath et al. | 435/5 |
| 4,929,543 | 5/1990 | Kientsch-Engel et al. | 435/5 |
| 5,122,446 | 6/1992 | Friedman-Kien | 435/5 |
| 5,122,468 | 6/1992 | Sarngadharan | 435/240 |
| 5,156,949 | 10/1992 | Luciw et al. | 435/5 |

FOREIGN PATENT DOCUMENTS

| | | | |
|---|---|---|---|
| 203443 | 12/1986 | European Pat. Off. | G01N 33/53 |
| 0217403 | 8/1987 | European Pat. Off. | 436/527 |
| 253464 | 1/1988 | European Pat. Off. | G01N 33/543 |
| 2099578 | 7/1985 | United Kingdom | G01N 33/543 |
| 2191578 | 12/1987 | United Kingdom | G01N 33/52 |
| WO84/04170 | 10/1984 | WIPO | G01N 33/54 |
| 88/07680 | 10/1988 | WIPO | G01N 33/53 |
| 193161 | 9/1986 | European Pat. Off. | C07K 15/00 |
| 0171150 | 12/1986 | European Pat. Off. | 435/7 |

OTHER PUBLICATIONS

Seradyn Current Inventory as of 16 Jul. 1990.

Boscato et al, "Incidence and Specificity of Interference in Two-Site Immunoassays", *Clin Chem*, vol. 32, No. 8 (1986) 1491-6.

Ottaviano et al, *Quality Control In The Clinical Laboratory: A Procederal Text*, (1977), pp. Xi and 3-5.

Beckman Instruments, Inc., ASTRA Automated STAT/Routine Analyzer Systems, Inslructions 015-246455A, May 1984, pp. 3-9.

Biological Abstract 79: 94949 (1985).

Biological Abstract 84: 104387 (1987).

Archibald, David W., et al. "Salivary Antibodies as a Means of Detecting Human T Cell Lymphotropic Virus Type III/Lymphadenopathy-Associated Virus Infection" (1986) *J. Clin. Microbiol.*, Nov., pp. 874-875.

Waldman, Alan A., and Calmann, Mark "Serum Creening for Anti-HTLV-III Antibodies. II: Screening Tests" (1986) *Laboratory Management*, pp. 31-34.

Marshall, David L. and Bush, Gerald A. "Latex particle enzyme immunoassay" (1987) *Immunoassay*, May/Jun., pp. 48-53.

Cao, Yunzhen, et al. "Detection of HIV Antigen and Specific Antibodies to HIV Core and Envelope Proteins in Sera of Patients With HIV Infection" (1987) *Blood*, 70:575-578.

Burke, Donald S., et al. "Diagnosis of Human Immunodeficiency Virus Infection by Immunoassay Using a Molecularly Cloned and Expressed Virus Envelope Oplypeptide" (1987) *Annals of Internal Medicine*, 106(5):671-676.

Chemical Abstracts, 106(9):65768h (1987).

*Chemical Abstracts*, 107(11):95143p (1987).

*Chemical Abstracts*, 107(17):152681p (1987).

Cao, Yunzhen, et al. "IgG Antibodies to HIV-1 In Urine of HIV-1 Seropositive Individuals" (1988) *The Lancet*, pp. 831-832.

Pottathil, Raveendran, et al. "Recombinant Antigens And Synthetic Peptides As Diagnostic Reagents For Detection Of Human Immunodeficiency Virus (HIV) Infection" (1988) *Medical Virology VII*, pp. 225-243.

Cao, Yunzhen "Detection of HIV-1 Specific Antibodies and Neutralizing Activity (NT Act.) In The Urine of Seropositive Persons" (1989), V International Conference on Aids.

Cao, Yunzhen, et al. "Antibodies to Human Immunodeficiency Virus Type 1 in the Urine Specimens of HIV-1-Seropositive Individuals" (1989) *Aids Research and Human Retrovirus*, 5:311-319.

Ng, Valerie L., et al. "Reliable confirmation of Antibodies to Human Immunodeficiency Virus Type I (HIV-1) with and Enzyme-Linked Immunoassay Using Recombinant Antigens Derived for the HIV-1 *gag, pol,* and *env* Genes" (1989) *J. Clin. Microbiol.*, 27(5):977-982.

(1962) A. Martin Lerner, et al., "Neutralizing Antibody to Polioviruses in Normal Human Urine," *Journal of Clinical Investigation*, 41(4):805-815.

(1972) S. De Donato, et al., "Sugli anticorpi antivirali delle urine," *Bollettino Dell'Istituto Sieroterapico Milanese*, 51(1):98-101, partial translation provided and *Chemical Abstracts*, 77(25):297-298, Abstract #86578u.

(1984) Thomas R. Trinick and Michael F. Laker, "Measurement of urinary immunoglobulins G, A and M by an enzyme linked immunosorbent assay (ELISA)," *Clinica Chimica Acta*, 139:113-117.

(List continued on next page.)

OTHER PUBLICATIONS (1986) D. W. Archibald, et al., "Antibodies to Human T-Lymphotropic Virus Type III (HTLV-III) in Saliva of Acquired Immunodeficiency Syndrome (AIDS) Patients and in Persons at Risk for AIDS," *Blood*, 67(3):831–834.

(1986) P. Hengster, et al., "HTLV-III in persons with intravenous drug abuse. Correlation of antibodies against HTLV-III with neopterin and TH/TS," *Dtsch. Med. Wochenschr*, 111(12):453–457, English Abstract Only.

*The Lancet*, Jun. 16, 1973, pp. 1346–1350, Alfred M. Prince, B. Brotman, D. Jass, and H. Ikram, "Specificity of The Direct Solid-Phase Radioimmunoassay For Detecting of Hepatitis-B Antigen."

*The Lancet*, Nov. 22, 1980, pp. 1136, W. M. Hunter and P. S. Budd, "Circulating Antibodies To OVine and Bovine Immunoglobulin In Healthy Subjects: A Hazard For Immunoassayas."

*Clin. Chem.*, 28(3):427–431 (1982), Peter J. Howanitz, Joan H. Howanitz, Harold V. Lamberson, and Kathleen M. Ennis, "Incidence and Mechanism of Spurious Increases in Serum Thyrotropin."

W. M. Hunter, J. G. Bennie, P. S. Budd, V. van Heyningen, K. James, R. L. Micklem, and A. Cott, "Immunoradiometric assays using monoclonal antibodies," in *Immunoassays For Clinical Chemistry*, 2nd edition, eds. W. M. Hunter and J. E. T. Corrie (Edinburg, London, Melbourne and New York: Churchill Livingstone, 12983), pp. 531–544.

*CCA*, (1985) Elsevier Science Publishers B. V. (Biomedical Division), Jay L. Bock, Joseph Furgiuele and Barry Wenz, "False positive immunometric assays coused by anti-immunoglobulin antibodies: a case report."

*Analytical Biochem.*, 146:393–401 (1985), Lynette M. Boscato, Gregory Egan, and Margaret C. Stuart, "Covert Gross Reactants in a Two-Site Immunoassay Studied with Monoclonal Antibodies."

*Clinical Chemistry, 31(2): 348–349 (1985), C. F. Cusick, K. Mistry, and G. M. Addison, Letter to the Editor regarding "Interference in a Tow-Site Immunoradiometric Assay for Thyrotropin in a child."*

*Clinical Chemistry*, 31(3):441–444 (1985), Jay L. Bock, Joseph Furgiuele, and Joseph C. Segen, "Choriogonadotropin Measured with the Tandem-E Immunoenzymetric Assay System."

*Clinical Chemistry*, 31(10):1762–1763 (1985), P. M. Clark, P. R. Raggatt, and C. P. Price, Letter to the Editor regarding "Antibodies Interfering in Immunometric Assays."

*Proc. Natl. Acad. Sci. USA*, 84:6924–6928 (Oct 1987), James R. Rusche, Debra L. Lynn, Marjorie Robert-Guroff, Alphonse J. Langlois, H. Kim Lyerly, Helen Carson, Kai Krohn, Annamarri Ranki, Robert C. Gallo, Dani P. Bologness, Scott D. Putney, and Thomas J. Matthews, "Humoral immune response to the entire human immunodeficiency virus envelope glycoprotein made in insect cells."

*Clin. Chem.*, 34(1):27–33 (1988), L. M. Boscato, and M. C. Stuart, "Heterophilic antibodies: a problem for all immunoassays."

5th International Conference on AIDS, Montreal, Canada (Jun. 4–9, 1989), Howard B. Urnovitz, I. Mitra, A. G. Govindarajan, T. Weiss, V. Haight, and T. Gottfried, "Sample, Easy to Use HIV-1 Recombinant Antigen Based Blood Antibody Test."

*Trends in Biotechnology*, 8:35–40 (1990), Toby D. Gottfried and Howard B. Urnovitz, "HIV-1 testing: product development strategies." (published in the U.K.).

*The Lancet*, 337:183–184 (Jan. 19, 1991), Shailesh Desai, Harold Bates, and Frank J. Michalski, "Detection of antibody to HIV-1 in urine."

MULTI-IMMUNOASSAY DIAGNOSTIC SYSTEM FOR ANTIGENS OR ANTIBODIES OR BOTH

This application is a continuation-in-part of U.S. Ser. No. 081,874, filed Aug. 5, 1987, now abandoned the contents of which are hereby incorporated by reference into the subject application.

FIELD OF THE INVENTION

This invention is in the field of immunodiagnostics. More specifically, this invention provides test strips, as well as kits containing, and methods employing, these strips for use in the immunological detection of analytes in aqueous liquids, particularly biological samples such as blood, urine, and the like.

BACKGROUND OF THE INVENTION

In recent years, the detection, or quantitative determination, or both, of analytes based upon reactions with immunological reagents has gained considerable importance, especially in the field of medical testing. Commonly, these methods involve contacting a sample suspected of containing the analyte with a material which exhibits specific immunologic reactivity with the analyte, for example, an antibody directed to an epitope present on the analyte. If the analyte is present in the sample, it specifically conjugates with the antibody to form a complex. A wide range of "developer" or "reporter" mechanisms have been proposed and are in use to indicate whether the conjugation reaction occurs. (See, for example, U.S. Pat. Nos. 4,366,242, issued Dec. 28, 1982 to Neumann, et al.; 4,278,653, issued Jul. 14, 1981 to Harris, et al.; and 4,208,479, issued Jun. 17, 1980 to Zuk, et al. )

Such methods have become increasingly popular since the introduction of monoclonal antibodies (MAbs), which may be produced using the technology developed by Kohler & Milstein, "Continuous Cultures of Fused Cells Secreting Antibody of Preferred Specificity," *Nature*, (1975) 256:495-7, and which have unique specificity for the analytes with which they conjugate. (See, for example, U.S. Pat. No. 4,376,110, issued Mar. 8, 1983 to David, et al.)

As these methods have evolved, there has been a parallel search for better ways to apply them on a day-to-day basis. This has led to a range of test devices, test kits, and the like. (See, for example, U.S. Pat. Nos. 4,623,461, issued Nov. 18, 1986 to Hossom, et al.; 3,888,629, issued Jun. 10, 1975 to Bagshawe; 4,458,020, issued Jul. 3, 1984 to Bohn, et al.; 4,496,654, issued Jan. 29, 1985 to Katz, et al.; and 4,305,924, issued Dec. 15, 1981 to Piasik, et al.) A majority of these devices utilize "flow through" membrane procedures for rapid testing (5-10 minutes). Often, the speed of the reaction does not allow enough time for critical thermodynamic controlled reactions to occur. The present invention provides a system to achieve equilibrium and thereby maximize the sensitivity of the test system.

Desirable characteristics of a test kit or device include the following:

1. The test device or kit should be easy to store and to use.
2. It should give unambiguous results without false positives or false negatives.
3. It should allow a multiplicity of samples to be screened in a short period.
4. Ideally, it should provide the user with positive indication that it has been used properly as confirmation that a false reading has not been obtained.
5. Preferably, it should allow a plurality of tests to be run simultaneously.
6. Preferably, the test can be configured to use whole blood, its fractionated components or urine.
7. Preferably, the test can be configured to allow the user to run equilibrium reactions.

It is a primary object of the present invention to provide a test strip and a test kit based thereon which provides these desirable features.

SUMMARY OF THE INVENTION

The present invention provides a test strip for detecting, in a sample from a human subject, the presence of an antigenic substance which comprises a solid support, an antibody directed against the antigenic substance bound to a first discrete area on the solid support, an anti-human antibody bound to a second discrete area on the solid support as a positive control, and an antibody directed against an antigen which does not naturally occur in human subjects bound to a third discrete area on the solid support as a negative control.

The present invention also provides a test strip for detecting, in a sample from a human subject, the presence of an antibody which comprises a solid support, an antigenic substance bound to a first discrete area on the solid support, an anti-human antibody bound to a second discrete area on the solid support as a positive control, and a negative control bound to a third discrete area on the solid support.

The invention additionally provides a test strip for detecting, in a sample from a human subject, the presence of an antibody and an antigenic substance which comprises a solid support, the antigenic substance bound to a first discrete area on the solid support, the antibody directed against an antigenic substance bound to a second discrete area on the solid support, an anti-human antibody bound to a third discrete area on the solid support as a positive control, an antibody directed against an antigen which does not naturally occur in human subjects bound to a fourth discrete area on the solid support as a negative control, and a second negative control bound to a fifth discrete area on the solid support.

The invention further provides a test strip for detecting the presence of an antibody and antigenic substance additionally comprising an antibody-based reagent directed against the antigenic substance in an immune complex and native human antibody thereto, bound to the second discrete area on the solid support. As a further embodiment, there may be other control areas on the solid support.

The invention also provides a method for detecting in a sample from a human subject the presence of an antigenic substance or antibody or both using the aforementioned test strips.

Thus, the present invention provides a test strip for immunologically detecting the presence of one or more analytes in aqueous specimens. The strip device comprises a solid support which has a plurality of discrete areas on its surface. One of these areas may include a test area which carries a monoclonal antibody (or a combination selected from polyclonal antibody, mono- or divalent antibody fragment, hybrid antibody, heterobifunctional antibody, or genetically manipulated or cloned antibody) to an analyte and may include an antigenic substance or both to be detected or quantitatively determined. This antibody or combination is preferably conjugated to, or immobilized on, the surface of the support. At least one of the discrete areas on the test strip carries a positive control, i.e., a control material which produces a positive signal only when the test area has been contacted with the specimen. In preferred embodiments this positive control is an immunological control, such that the control event includes an immunological reaction between a species always present in the specimen and its immunologically specific partner immobilized in the positive control zone.

In other preferred embodiments, this test strip includes at least one area carrying a negative control, that is, a control material which does not give rise to a detectable event in the presence of a normal specimen but does give rise to a detectable event when the sample is abnormal.

In another preferred embodiment, the sample is urine.

In another embodiment, this test strip contains a plurality of separate test areas containing different antibodies or combinations of antibodies so as to detect more than one analyte in the specimen.

In another embodiment, this test strip contains a plurality of separate test areas containing different analytes or combinations of analytes to detect antibody or other analytes.

In yet another embodiment, this invention provides a test kit. This test kit includes the test strip just described and a test plate comprising a plurality of liquid holders, each shaped and sized to receive the test strip and to permit the test areas and positive control zone and negative control zone to simultaneously contact each of a sequence of liquids which are predeposited in the holders and at least one of which includes the test specimen.

In a presently preferred embodiment of this kit, the test plate comprises a plurality of liquid holders so as to permit a plurality of specimens to be tested at the same time, using a plurality of test strips.

DETAILED DESCRIPTION OF THE INVENTION

This invention provides a test strip for detecting, in a sample from a subject, particularly a human subject, the presence of an antigenic substance. This test strip comprises a solid support, an antibody directed against the antigenic substance bound to a first discrete area on the solid support, an anti-human antibody bound to a second discrete area on the solid support as a positive control, and an antibody directed against an antigen which does not naturally occur in human subjects bound to a third discrete area on the solid support as a negative control. Such a test strip may also be readily adapted so as to quantitatively determine the amount or concentration of the antigenic substance present in the sample.

It would be expected by one skilled in the art that more than one antigenic substance could be detected using a single test strip.

This invention also provides a test strip for detecting, in a sample from a subject, particularly a human subject, the presence of an antibody. This test strip comprises a solid support, an antigenic substance bound to a first discrete area on the solid support, an anti-human antibody bound to a second discrete area on the solid support as a positive control, and a negative control. Such a test strip may also be readily adapted so as to quantitatively determine the amount or concentration of the antibody present in the sample. The negative control may be but is not limited to a blocking solution or a recombinant antigen which does not naturally occur in human subjects.

It would be expected by one skilled in the art that more than one antibody could be detected using a single test strip.

This invention also provides a test strip for detecting, in a sample from a subject, particularly a human subject, the presence of an antibody and an antigenic substance. This test strip comprises a solid support, the antigenic substance bound to a first discrete area on the solid support, an antibody directed against an antigenic substance bound a second discrete area on the solid support, an anti-human antibody bound to a third discrete area on the solid support as a positive control, and an antibody directed against an antigen which does not naturally occur in human subjects bound to a fourth discrete area on the solid support as a negative control. Such a test strip may also be readily adapted so as to quantitatively determine the amount or concentration of the antigen which substance and antibody present in the sample. As a further embodiment, there may be other control areas on the solid support which may or may not be blocking solution alone.

It would be expected by one skilled in the art that more than one antigenic substance and antibody could be detected using a single test strip.

This invention also provides a test strip which comprises all of the elements of the aforementioned test strip for detecting the presence of an antigenic substance and antibody and additionally comprising an antibody-based reagent directed against the antigenic substance in an immune complex and native human antibody thereto, bound to the second discrete area on the solid support.

In one embodiment of this invention, the antigenic substance being detected is a virus or a viral protein. For example, the antigenic substance may be HIV-1 GAG protein, HIV-1 ENV glycoprotein, HIV-1 POL protein, HIV-2 GAG protein, HIV-2 ENV glycoprotein, HIV-2 POL protein, HTLV-1 GAG protein, HTLV-1 ENV glycoprotein, and HTLV-1 POL protein and Hepatitis B surface antigen or its epitope therewith.

In a preferred embodiment, a plurality of antibodies to analytes is detected, which in a particularly preferred embodiment includes antibodies to HIV-1, HIV-1 GAG protein, HIV-1 ENV glycoprotein, HIV-1 POL protein, HIV-2, HIV-2 GAG protein, HIV-2 ENV glycoprotein, HIV-2 POL protein, HTLV-1, HTLV-1 GAG protein, HTLV-1 ENV glycoprotein, HTLV-1 POL protein, a Hepatitis B core antigen, or an epitope thereof.

In another preferred embodiment a plurality of both analytes and antibodies to analytes is simultaneously detected, which in a particularly preferred embodiment detects HIV-1 GAG protein and antibodies to HIV-1 ENV glycoprotein or in another particularly preferred embodiment the simultaneous detection of Hepatitis B surface antigen and antibodies to Hepatitis B core antigen.

In test strips according to this invention, the solid support may comprise glass fiber filter paper, nitrocellulose, scintered glass, plastic, synthetic polymer, cellulose, cellulose acetate, polystyrene, polytetrafluoroethylene, polyethylene, polypropylene, or polyvinylidine fluoride.

In certain embodiments of this invention involving an antibody-based reagent, this reagent comprises a monoclonal antibody, polyclonal antibody, mono- or divalent antibody fragment, hybrid antibody, heterobifunctional antibody, or genetically manipulated or cloned antibody. Heterobifunctional antibodies are described by Urnovitz, et al. in "IgA:IgM and IgA:IgA Hybrid Hybridomas Secrete Heteropolymeric Immunoglobulins that are Polyvalent and Bi-Specific", *J. Immunol.*, 140:558–563 (1988).

In a preferred embodiment of this invention the antihuman antibody on the test strip is, but is not limited to, a monoclonal antibody.

Similarly in a preferred embodiment of this invention, the antigen which does not naturally occur in human subjects and which is present on the test strip is, but is not limited to, a synthetic organic molecule, e.g., dinitrophenol.

In preferred embodiments of this invention one or more of the anti-human antibody, the antibody directed against an antigen, or the antibody-based reagent is labeled, for example, with a radioactive isotope, fluorophore, chromophore, or a ligand which can be used with an enzyme that catalyzes a chemical reaction which produces a detectable product that can be further amplified in a secondary reaction.

The invention further provides a method for detecting in a sample from a human subject the presence of an antigenic substance which comprises pretreating the sample to be tested so as to prevent simultaneously non-specific and specific binding of substances present in the sample to proteins, including antibodies, present on the test strip, and thus prevent spurious results, contacting the resulting pretreated sample with the test strip for detecting an antigenic substance under conditions such that the antibody directed against the antigenic substance bound to the test strip forms a complex with antigenic substance thereafter treating the test strip to remove uncomplexed antibody, contacting the resulting, treated test strip with labeled antibody to the antigenic substance under conditions such that the labeled antibody forms a complex with the antigenic substance complexed to the antibody bound to the test strip, detecting the presence of labeled antibody complexed to the test strip, and thereby the presence of the antigenic substance in the sample, and verifying the correctness of the detection so made by means of the positive and negative controls on the test strip.

The invention additionally provides a method for detecting in a sample from a human subject the presence of a human antibody directed to an antigenic substance which comprises pretreating the sample to be tested so as to prevent simultaneously non-specific and specific binding of substances present in the sample to proteins, including antigenic substances, present on the test strip, and thus prevent spurious results, contacting the resulting pretreated sample with the test strip for detecting an antibody under conditions such that the antigenic substance bound to the test strip forms a complex with any human antibody directed against it which is present in the sample, thereafter treating the test strip to remove uncomplexed antibody, contacting the resulting, treated test strip with labeled antihuman antibody under conditions such that the antihuman antibody forms a complex with any human antibody complexed to the test strip, detecting the presence of labeled antihuman antibody complexed to the test strip, and thereby the presence of human antibody in the sample, and verifying the correctness of the detection so made by means of the positive and negative controls on the test strip.

The invention additionally provides a method for detecting in a sample from a human subject the presence of an antigenic substance and a human antibody directed to an antigenic substance which comprises pretreating the sample to be tested so as to prevent simultaneously non-specific and specific binding of substances present in the sample to proteins, including antibodies and antigenic substances, present on the test strip, and thus prevent spurious results, contacting the resulting pretreated sample with the test strip for detecting the presence of an antigenic substance and antibody under conditions such that the antibody directed against the antigenic substance bound to the test strip forms a complex with the antigenic substance and the antigenic substance bound to the test strip forms a complex with any human antibody directed against it which is present in the sample, thereafter treating the test strip to remove uncomplexed antibody, contacting the resulting, treated test strip with labeled antibody to the antigenic substance and labeled antihuman antibody under conditions such that the labeled antibody forms a complex with the antigenic substance complexed to the antibody bound to the test strip and the antihuman antibody forms a complex with any human antibody complexed to the test strip, detecting the presence of labeled antibody and labeled antihuman antibody complexed to the test strip, and thereby the presence of the antigenic substance and human antibody in the sample, and verifying the correctness of the detection so made by means of the positive and negative controls on the test strip.

In preferred embodiments of the invention the hereinabove described method involves as the antigenic substance, a virus or viral protein, and as the sample, blood, serum, or the like. In a particularly preferred embodiment, the sample is urine.

The invention also provides the aforementioned methods wherein the verification comprises contacting the test strip with labeled antihuman antibody under conditions such that the labeled antihuman antibody binds to human antibody bound to the test strip.

Thus, the present invention provides an improved test strip device. One embodiment of this device is shown as 10 in FIG. 1. It includes a solid support 11 having a plurality of readable areas 12, 14 and 15. While support 11 is shown as a solid "dip stick" structure, it can be virtually any geometric shape, including cube, block, rod, cylinder, prism, polygon, spiral, sphere or segmented combinations thereof. It can also be a carrier device holding materials such as plastic, metal, paper, or the like. It can be made of a wide range of materials including plastic, such as polystyrene or the like; metal; paper; glass fiber filter paper; nitrocellulose; scintered glass; synthetic polymers; cellulose; cellulose acetate; polystyrene; polytetrafluoroethylene; polyethylene; polypropylene; polyvinylidine fluoride; or any other material including the materials which it comes in contact with during the test. Commonly, the materials deposited on its surface are adsorbed, chemically coupled, or otherwise bound to the surface of the test strip as described hereinafter.

Figure 1:
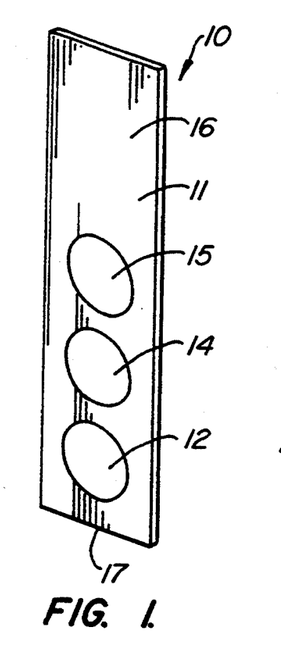
FIG. 1 is a perspective view of a test strip in accordance with the invention, showing its various zones or areas in semischematic form.

Readable areas 12, 14 and 15 are arrayed separately on support 11 so as to give a plurality of potential signals when the strip is processed in the analysis method. The readable area may include antibody which is immunoreactive with a test analyte in the test specimen or antigenic substance. The readable areas may also include an analyte reactive with test antibody or test analyte. At least one of the readable areas includes a positive control which reacts with a test specimen to verify via a detectable signal when the test strip properly contacts a test specimen. Preferably, this positive control is an immunologic positive control which undergoes immunologic reaction with a nonanalyte species in the specimen.

The readable areas can also include a negative control, namely, a discrete area containing one or more reagents that do not produce a reading with the specimen if the specimen is properly handled but which do give a reaction and produce a signal if the specimen is defective or has been mishandled.

The relative position of the positive control area and the antibody-containing areas may be important. Test strip 10 is used as a "dip stick." In use, the technician or automated test device grips or "holds" the strip by top end 16 and dips it into the liquid specimen and other reagents, lower end 17 first. This means that area 12 will contact these liquids before area 15 does. It is desirable, therefore, that the positive control, which gives a positive reading only when the specimen and reagents have properly contacted it be positioned as the last to be contacted or uppermost area, e.g., 15 in FIG. 1. Conversely, the negative control, if present, should be positioned as the first to be contacted or bottommost, e.g., 12 in FIG. 1.

The positive control and the negative controls are preferably immunologic. That is, they preferably function by means of immunological reactions. Thus, for example, when the test specimens are human serum-based, a typical positive control could be a region designed to be treated with a common immunoglobulin always found in blood or its fractionated components.

The test reagent region (14 in FIG. 1) is based on and may include an antibody specific for the analyte being tested for or an antigenic substance. A wide range of antibodies against a wide range of potentially important analytes have been described in the literature and may be used.

Figure 2:
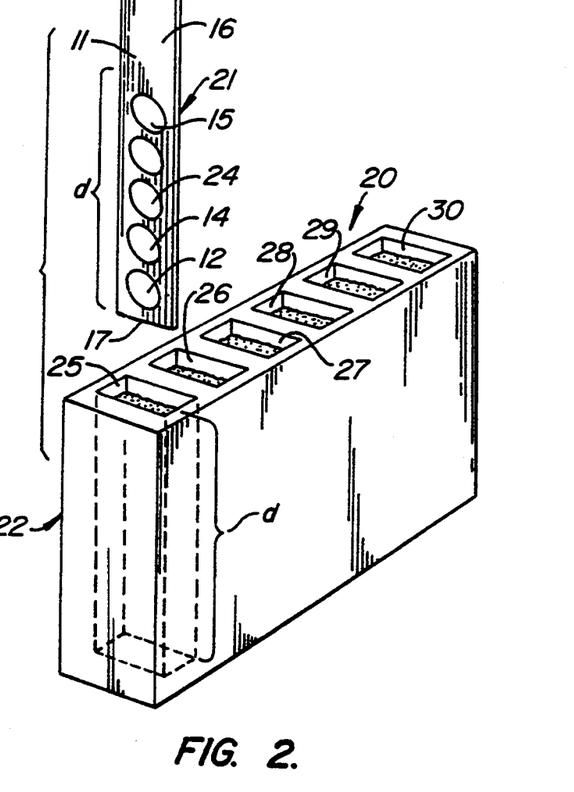
FIG. 2 is a perspective and semischematic view of another embodiment of a test strip of this invention, together with a sample test plate.

Turning to FIG. 2, a variation on the test strip of FIG. 1 is shown as 21. Strip 21 is shown as part of an overall analysis kit 20 which also includes a test plate 22. Strip 21 includes support 11 and readable areas 12, 14 and 15 as previously described and an additional readable area 24. Area 24 may be an additional control, an analyte, or an additional antibody-containing test region. Area 24 may contain a second antibody against the same antigen of area 14 so as to provide additional confirmation or sophistication to the test result or it may contain an antibody against a second antigen-analyte. These various reagents are generally immobilized in their various regions to prevent cross-contamination and the like, which will give ambiguous results. Antibody or most analytes are commonly immobilized on plastics, carbohydrate polymers, adsorbent fibers, polymer-coated metal beads, silica gel, paper, glass filters, or the like, by either direct adsorption (incubation for limited times or until the reagent solution is completely dry) or by chemical coupling to reactive groups on the solid phase. The optimal conditions are unique for each reagent.

In a typical application, the test strip 21 is employed in concert with a test plate such as 22. Test plate 22 has several characteristics. For one, it contains a plurality of liquid storage wells such as 25, 26, 27, 28 and 29. The exact number is selected to accommodate the various steps required to effect the desired assay sequence. For another, the size of each of the wells is set so as to permit the strip to be inserted. For another, the wells are deep enough to accommodate a depth of liquid "d" which is a depth adequate to completely cover all the readable areas 12, 14 and 15; or 12, 14, 24 and 15, present on the test strip.

In use, one or more of the wells of test plate 22 are charged with predetermined quantities of reagents and samples according to a predetermined protocol and then the test strip is inserted into the wells, again according to a predetermined protocol. This gives rise to a readable detection event which is read together with the results of the positive and negative controls. On the basis of these readings, one may determine whether a valid test has been conducted and whether the analyte is present in the specimen.

For example, in a typical protocol a test strip might be constructed with an antibody against a suspected pathogen in human blood. Positive control 15 would have an antibody against a common blood constituent, and negative control 12 would have an antibody against a material not commonly found in blood but of concern as a contaminant, or the like.

Well 25 is charged with a premeasured quantity of diluent, buffer or a like aqueous medium. A given quantity of patient blood or other source is added to the liquid of well 25 and mixed with it. The strip is inserted into the liquid in well 25 for a preset interval. This permits the test and control areas on strip 21 to contact the liquid and the diluted blood constituents. This allows the immunological reactions to occur between the antibodies in these areas and any appropriate species in the blood.

The sample well 25 and any other well may contain various reagents to prevent undesired reactions and the like. These may include materials so as to alter the properties of the sample, or materials to react with or remove undesired cross-reactive materials in the samples.

A current problem with most immunodiagnostic assays is the undesirable interaction of sample constituents with the coated solid phase (i.e. background). These types of interaction often cause negative samples to be interpreted as false positives. Background may be minimized by partitioning the undesirable reactants (specific and nonspecific) onto a second solid phase (usually by preincubating the sample before exposure to the test solid phase). In the case of human antibody capture assays, the second solid phase would have bound to it antibody specific for an analyte not found in the sample or test (i.e., irrelevant specificity) and/or non-human blood components to reduce heterophile antibody contamination and the like. This type of second solid phase would remove both specific and nonspecific background constituents for antibodies, the solid phase, the blocking reagent, or a combination of any of the three. The second solid phase may be used in any or all parts of the assay although preferably eliminated at the "developer" stage. In the case of human derived viral components as analyte, preinfected human components may be used as adsorbent reagent for the second solid phase partitioning. In addition, a third solid phase could be envisioned to add another dimension of background reduction.

The configuration for the second phase should be designed for the mechanics of the reaction. Adsorbent reagents would coat the chamber walls of the sample tray for some solutions. For rapid immunoassay, a critical step in controlling background is the initial mixing of solid phase and sample. The second solid phase should be free to move within the mixing solution (a second strip of any geometric shape or particles). A preferred method would employ an adsorbing means comprising a suspension of particle beads (approximate diameter of 0.5 to 10 micrometers) or any or all of the chambers into which the test strip is immersed. The advantage is a large total surface area for rapid reaction kinetics and maximum diffusion of reactants. Preincubation of sample with adsorbent coated particles would quickly remove background components before exposure to the test strip. Preparation of these types of particles is described in the examples. The third solid phase could be the chamber walls of the sample tray for some solutions.

Next the test strip is removed from well 25 and inserted into well 26. Well 26 may contain, for example, a premeasured quantity of a wash solution to remove interfering materials, or the like. Thereafter, the test strip is passed to a well 27 containing a detection system, for example, a labeled antibody, or a labeled antibody to the bound antigen or the like. Next, the strip may be moved to well 29 for washing and finally to well 30 where a substrate (e.g., chromogenic reagent) is added or already present. In some cases, excess liquid on the strip may be removed and substrate added directly to the strip. Other wells may be present to contain other reagents as required or desired.

Figure 3:
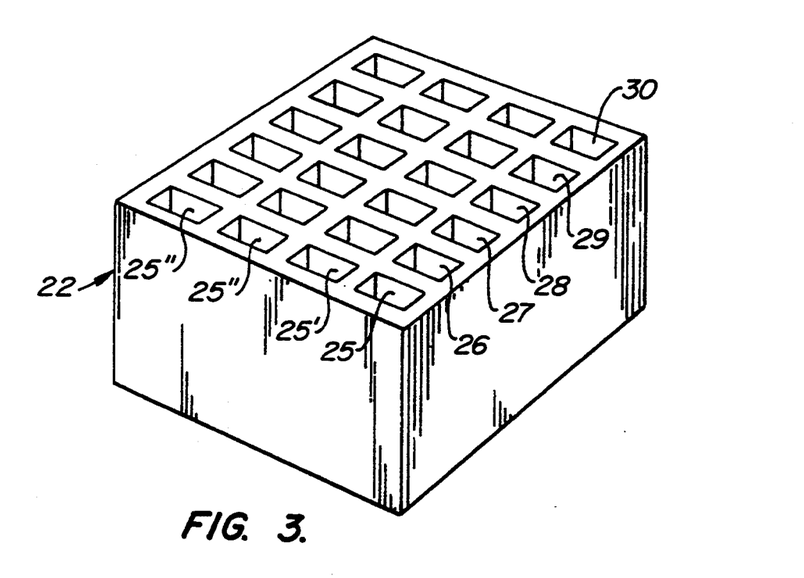
FIG. 3 is a perspective view of a test plate adapted to permit multiple specimens to be tested simultaneously.

FIG. 3 illustrates an extension of the invention in which test block 22 includes a plurality of sets (i.e., 4 sets) of wells so that there are four sample wells 25, four wash wells 26, etc. This permits multiple samples to be tested at once with multiple test strips.

Figure 4:
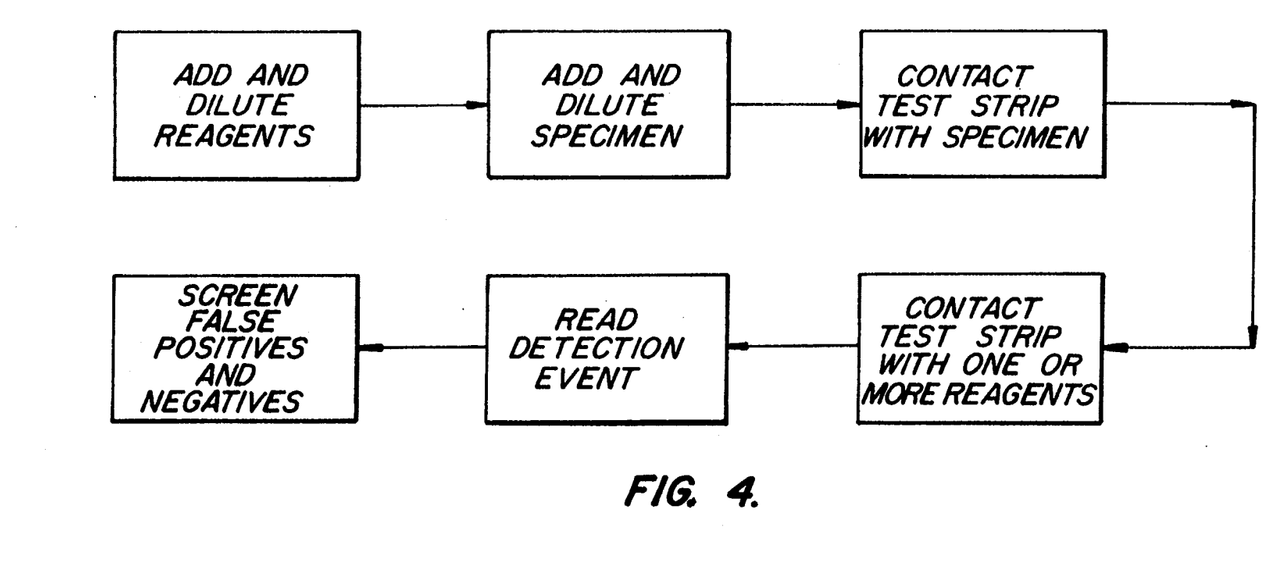
FIG. 4 is a block diagram of a typical test protocol which may be employed according to the present invention.

FIG. 4 provides a block diagram of the typical test protocol just set forth and points out the sequential nature of the test method.

It will be appreciated by those skilled in the art that this invention is not limited to particular antigenic substances, particular antibodies, reagents, particular samples, or particular utilization chemistries and that reasonable alternatives may be employed without departing from its teachings.

It should be noted that suitable antibodies for use in the test reagent region(s) may be monoclonal antibodies, polyclonal antibodies, mono- or divalent antibody fragments, hybrid antibodies, heterobifunctional antibodies, or genetically manipulated or cloned antibodies.

The test itself is, as noted above, a method of immunologically detecting the presence of one or more analytes in a specimen. Typically, the test is used in either the detection or the quantitation of bound or unbound label, wherein the amount of label detected corresponds to the amount of analyte in the specimen. As used herein, the "immunoassay procedure" of the subject invention may be in the nature of immunoelectron microscopy or fluorescence polarization, or it may be an immuno-fluorescent assay, a radiometric assay, an enzyme-linked immunoassay, or a photon-counting bioluminescent or chemiluminescent assay. The assay can be comprised of a secondary system which amplifies a ligand attached to the antibody. In the case of the enzyme-linked immunoassay, the enzyme used is normally selected from the group consisting of alkaline phosphatase, glucose oxidase, horseradish peroxidase, urease, luciferase, and galactosidase. The label itself may be virtually any detectable species, e.g., a chromogenic compound, a radioactive isotope, an enzyme, or a fluorescent, luminescent, bioluminescent, chemiluminescent, phosphorescent, or ferromagnetic material.

The analyte may be virtually any compound or organism which is detectable using the aforementioned procedure, i.e., a drug, hormone, vitamin, enzyme, ligand, protein, including glycoprotein and lipoprotein, antibody, polysaccharide, cell or tissue antigen, or bacterium, protozoan, parasite, fungus, virus, blood cell substance, blood fluid substance, or a component of any of the foregoing. In a preferred embodiment, a plurality of analytes is detected, which in a particularly preferred embodiment includes HIV-1 GAG protein, HIV-1 ENV glycoprotein, HIV-1 POL protein, HIV-2 GAG protein, HIV-2 ENV glycoprotein, HIV-2 POL protein, HTLV-1 GAG protein, HTLV-1 ENV glycoprotein, HTLV-1 POL protein and Hepatitis B core protein purified from natural isolates, recombinant genetic manipulations or chemical synthesis.

The aforementioned analytes may also be bound to the test strip as the actual detecting reagents in alternative assay procedures.

The specimen may be blood or its fractionated components, urine, saliva, vaginal fluid, seminal fluid, mucosa, birth fluids, tears, gastrointestinal fluid and excrement, inflammatory fluids, pleural effusion, pulmonary fluid, tissue extracts and the like derived from mammalian, avian, reptilian, amphibian, arthropod and the like sources.

In alternative embodiments, the specimen or sample to be tested may be an industrial sample, e.g. industrial waste chemicals or water, and the analyte may be an industrial pollutant or toxic chemical present therein.

The invention is further illustrated by the following examples which are not intended to and should not be construed so as to limit in any way the scope of the invention as defined by the claims which follow thereafter.

EXAMPLE 1

Detection of Human Anti-HIV-1 Antibody in One Assay Minimization of False Positives I. Preparation of the Test Stick Test strip prototypes were constructed from the lids of 96-well tissue culture plates (Costar, catalog #3096). Strips were cut from the lid using a sharp knife attachment on a soldering iron so that the strip contained 8 contiguous circles, each surrounded by a raised peripheral ring. Strips can also be used as support segments to contain highly adsorbent solid phase (e.g., Nylon membrane or nitrocellulose paper). The strip was washed in a buffer and allowed to air dry.

Monoclonal antibodies, designated DNP1 (CB6 mouse IgG1, specific for dinitrophenol) and anti-HIgG (CB6 mouse IgG1, specific for human immunoglobulin G) were gifts from Dr. Pao-Min Loh's laboratory (University of Iowa). Anti-HIV GAG (mouse IgG1, specific for Human Immunodeficiency Virus-1) was purchased from Epitope, Inc. (catalog #5001). Cocktails of MAbs with specificity for each analyte can be used. Here, the MAbs were made 100 micrograms/ml in Tris Buffered Saline (TBS, 0.15M NaCl, 0.05M Tris, pH 7.2) and 10 microliters was applied directly to designated circular segments. HIV-1 (Litton Bionetics, HTLV-3, cat. #37225, 1 milligram/ml, NP40 inactivated) was made 2 micrograms/ml in TBS. 10 microliters were applied directly to the designated circular segment. The ordering of reagents was as follows:

Anti-human IgG (positive control) [top]
Anti-HIV GAG (detects virus antibody complex)
HIV-1 (detects antibody)
Anti-DNP (negative control) [bottom]

The stick was placed horizontally (solution side up) into a 45° C. oven and the antibody and antigen allowed to dry for about 30 minutes. The stick was placed in blocking solution (TBS with 0.3% TWEEN™, polyoxyethylenesorbitan monolaurate, Sigma Chemical Company, 1 mg/ml bovine serum albumin, BSA, and 0.1% sodium azide) for a minimum of 15 minutes.

II. Preparation of Adsorbent Beads

To minimize the contribution of certain samples' affinity to bind to proteins denatured on solid surfaces (or solid surfaces directly), latex polystyrene particles were covalently coupled with monoclonal anti-DNP antibody (purified human T-cell plasma membrane can also be coupled to latex particles when viral analyte is either directly adsorbed or chemically coupled). In addition, the nonspecific adsorbent can be coated on any other solid phase or directly onto the walls of the chamber. Antibody is made 200 micrograms/ml in PBS (0.1M phosphate-buffered saline, pH 7.2, Pandex Laboratories published Research Report, No. 4 (1984) "Coupling of Antigens to Latex Particles by the Water-Soluble Carbodiimide Method," by Michael E Jolley, Ph.D.). The antibody solution was added to washed and pelleted latex particles (Pandex, Epicon carboxyl-polystyrene particles, catalog #31-010-1). The solution was triturated and exposed to 20 sec of an ultrasonic water bath. The final concentration of beads was 0.5%. Solid carbodiimide (Sigma, 1-ethyl-3-[3-dimethylaminopropyl]-carbodiimide, catalog #E-7750) is added to make a final concentration of about 5 milligrams/ml. The solution is rotated gently for one hour at room temperature and washed (with PBS) and pelleted (12,000×g, 3 min. room temperature) three times. The final bead solution is made 0.01% to 0.5% (w/v) in blocking buffer.

III. Sample Tray

A sample tray was configured by solvent welding plastic cuvettes (Elkay Products, catalog #127-1010-400) with a cyanoacrylate glue. The cuvettes were 1 cm×1 cm×4.5 cm. In this example, the tray contains 7 cuvettes (with lids). In this example, the first compartment contained 2.5 ml of an approximately 1.0 micrograms/ml, inactivated HIV-1 (Litton Bionetics, HTLV-3, cat. #37225, 1 milligram/ml, NP40 inactivated) in blocking buffer containing about 0.1% adsorbent beads described above. The second compartment contained 2.5 milliliters wash solution (TBS/0.3% TWEEN™, polyoxyethylenesorbitan monolaurate, Sigma Chemical Company). The third compartment contained a mixing solution (2.5 milliliters of blocking solution with about 0.1% adsorbent beads) for diluting the human blood specimen. The fourth compartment contained 2.5 milliliters wash solution (TBS/0.3% TWEEN). The fifth compartment contained 2.5 milliliters of developing conjugate solution; polyclonal goat anti-human immunoglobulin coupled to alkaline phosphatase (Jackson Immunoresearch Labs, catalog #109-5576) diluted 1:500 in blocking solution with about 0.1% adsorbent beads. The sixth compartment contained 2.5 milliliters of wash solution (TBS/0.3% TWEEN™). The seventh compartment contained 2.5 milliliters of presubstrate wash "solution (pH 10 alkaline buffer).

IV. The Assay

The lid for chamber #3 was removed. A drop of blood (obtained by a lancet puncture to a finger, alternatively, 1 to 50 microliters of serum may be used) was allowed to drip into the third compartment. With each chamber covered with its respective lid, the entire tray was gently shaken several times to ensure mixing of blood and bead solution. The tray was returned to its original standing position and the lid removed from chamber #1. While the blood was incubating in chamber #3, a test strip was immersed in chamber #1. The solution was gently stirred with the test strip and allowed to incubate at 42° C. for about 20 minutes. Care was taken to ensure that the readable area was maximally exposed to the solvent phase. The strip was transferred to compartment #2 and washed for about 10 seconds. The strip was transferred to compartment #3 containing the blood/adsorbent mixture. The solution was gently mixed and allowed to incubate with the strip for about 30 minutes at 42° C. The strip was transferred to compartment #4 and washed for about 10 seconds. The strip was transferred to compartment #5. With about 5 seconds of gentle stirring, the strip was allowed to incubate (stirring every 1 min.). After a total of about 10 minutes incubation, the strip was transferred to compartment #6 and gently stirred for about 10 seconds. The strip was transferred to compartment #7 and washed for about 10 seconds. The strip was removed and tapped lightly to remove excess liquid. One drop (about 50 microliters) of substrate (5-bromo-4-chloro-3-indolyl phosphate, Sigma catalog #B-0766, in alkaline buffer, pH 10) was added to each readable area. After approximately 10 minutes, the color reaction of each readable area was recorded as positive (blue color) or negative (no color).

V. Interpretation The assay can only be valid if the segment containing the anti-DNP MAb (negative control) remains colorless. The adsorbent beads should remove all materials that cause a false positive reaction and the negative control readable area was used to confirm this function. The anti-HIgG segment should bind human immunoglobulin present in blood samples. This reaction must be positive or else the test reagents are not working, thus invalidating the test. A positive blue color in the HIV-1 segment indicates that there is antibody to HIV-1 present in the blood sample. A positive response in the anti-HIV segment suggests that virus is present complexed with human anti-HIV antibody.

EXAMPLE 2

Detection of Human Anti-HIV-1 Antibody Minimization of False Positives

I. Preparation of the Test Stick

Test strip prototypes were constructed from the lids of 96-well tissue culture plates (Costar, catalog #3096). Strips were cut from the lid using a sharp knife attachment on a soldering iron so that the strip contained 8 contiguous circles, each surrounded by a raised peripheral ring. Strips can also be used as support segments to contain highly adsorbent solid phase (e.g., Nylon membrane or nitrocellulose paper), also, sticks can be constructed in such a way that can contain recessed reactive areas. The strip was washed in a buffer and allowed to air dry.

Monoclonal antibodies, designed DNP1 (CB6 mouse IgG1, specific for dinitrophenol) and anti-HIgG (CB6 mouse IgG1, specific for human immunoglobulin G) were used. Cocktails of MAbs with specificity for each analyte can be used. Here, the MAbs were made 100 micrograms/ml in Tris Buffered Saline (TBS, 0.15M NaCl, 0.05M Tris, pH 7.2) and 10 microliters applied directly to designated circular segments. HIV-1 (Litton Bionetics, HTLV-3, cat. #37225, 1 milligram/ml, NP40 inactivated) was made 2 micrograms/ml in TBS. 10 microliters were applied directly to the designated circular segment. The ordering of reagents was as follows:

Anti-human IgG (positive control) [top]
HIV-1 (detects antibody) [middle]
Anti-DNP (negative control) [bottom]

The stick was placed horizontally (solution side up) into a 45° C. oven and the antibody allowed to dry for about 30 minutes. The stick was placed in blocking solution (TBS with 0.3% TWEEN TM, 1 mg/ml bovine serum albumin, BSA, and 0.1% sodium azide) for a minimum of 15 minutes.

II. Preparation of Adsorbent Beads

To minimize the contribution of certain samples' affinity to bind to proteins denatured on solid surfaces (or solid surfaces directly), latex polystyrene particles were covalently coupled with monoclonal anti-DNP antibody (purified human T-cell plasma membrane or recombinant DNA related proteins such as beta-galactosidase can also be coupled to latex particles when viral analyte is either directly adsorbed or chemically coupled). In addition, the non-specific adsorbent can be coated on any other solid phase or directly onto the walls of the chamber. Antibody is made 200 micrograms/ml in PBS (0.1M phosphate-buffered saline, pH 7.2, Pandex Laboratories published Research Report, No. 4 (1984) "Coupling of Antigens to Latex particles by the Water-Soluble Carbodiimide Method," by Michael E. Jolley, Ph.D.). The antibody solution was added to washed and pelleted latex particles (Pandex, Epicon carboxyl-polystyrene particles, catalog #31-010-1). The solution was triturated and exposed to 20 sec of an ultrasonic water bath. The final concentration of beads was 0.5%. Solid carbodiimide (Sigma, 1-ethyl-3-[3-dimethylamino-propyl]-carbodiimide, catalog #E-7750) is added to make a final concentration of about 5 milligrams/ml. The solution is rotated gently for one hour at room temperature and washed (with PBS) and pelleted (12,000×g, 3 min., room temperature) three times. The final bead solution is made 0.01% to 0.5% (w/v) in blocking buffer.

III. Sample Tray

A sample tray was configured by solvent welding plastic cuvettes (Elkay Products, catalog #127-1010-400) with a cyanoacrylate glue. The cuvettes were 1 cm×1 cm×4.5 cm. In this example, the tray contains 6 cuvettes (with lids). The first chamber contained a mixing solution (2.5 milliliters of blocking solution with about 0.1% adsorbent beads) for diluting the human blood specimen. The second chamber contained 2.5 milliliters wash solution (TBS/0.3% TWEEN TM). The third chamber contained 2.5 milliliters of developing conjugate; polyclonal goat anti-human immunoglobulin coupled to alkaline phosphatase (Jackson Immunoresearch Labs, catalog #109-5576) diluted 1:500 in blocking solution. The fourth chamber contained 2.5 milliliters of wash solution (TBS/0.3% TWEEN TM). The fifth chamber contained 2.5 milliliters of presubstrate wash solution (pH 10 alkaline buffer). The sixth chamber contained 1 ml of substrate solution (5-bromo-4-chloro-3-indolyl phosphate, Sigma catalog #B-0766, in alkaline buffer, pH10).

IV. The Assay

The sample tray was equilibrated in a 42° C. water bath. 5 microliters (5-200 microliters can be used) of serum or plasma was added into the first chamber. The sample in chamber 1 was allowed to incubate for 3 minutes at 42° C. (40°-45° C. may be used). The solution was gently stirred with the test strip and allowed to incubate at 42° C. for about 45 minutes. Care was taken to ensure that the readable area was maximally exposed to the solvent phase. The strip was transferred to chamber #2 and washed for about 1-10 seconds. The strip was transferred to chamber #3. With about 5 seconds of gentle stirring, the strip was allowed to incubate at 42° C. for about 45 minutes. The strip was transferred to chamber #4 and gently stirred for about 1-10 seconds. The strip was transferred to chamber #5 and washed for about 1-10 seconds. The entire sample tray was removed from the 42° C. water bath and placed on the bench at room temperature. The strip was transferred to chamber #6 and allowed to incubate at room temperature for 10-20 minutes. The color reaction of each readable area was recorded as positive (blue color) or negative (no color).

Three double-blind studies were performed to determine the presence of antibodies to HIV-1 in patient serum.

Test A: 25 out of 50 serum samples (Peralta Cancer Center, Oakland, Calif.) were Western Blot (WB) positive for HIV-1 antibodies (predominantly gp41 only). The other 25 were from a WB negative donor serum pool. The test accurately identified 100% of the samples as negative or positive as compared with the WB results.

Test B: 21 HIV-1 WB positive blood samples, and 7 false positive blood samples (as originally screened on the Abbott HIV-1 antibody test at the Massachusetts General Hospital Blood Bank, Boston, Mass.) were tested with the test. In the test, all 21 WB positive samples were confirmed along with the 23 WB negative samples. All 7 false positive samples were negative by the test.

Test C: 9 HIV-1 WB positive blood samples (NYU Medical Center) and 10 WB negative blood samples were correctly identified by the test. Two HIV-1 antibody positive semen samples, two saliva samples and 1 urine sample were also positive in the test.

EXAMPLE 3

Detection of HIV-1 P24 Antigen in Patient's Serum

I. Preparation of the Test Sticks

Test sticks are the same as those in Example 1. The following monoclonal antibodies are adsorbed to the stick: 1F8 (Calypte Biomedical Company's anti HIV-1 GAG monoclonal antibody, IgG1); anti-HIgG and anti-DNP. Here, the MAbs were made 100 milligram/ml in Tris Buffered Saline and 10 microliters applied directly to a designated circular segment. The ordering of MAbs was as follows:

Anti-Human IgG (positive control) [top]
Anti-HIV GAG (detects P24) [middle]
Anti-DNP (negative control) [bottom]

The stick was placed horizontally solution side up into a 45° C. oven and antibodies allowed to adsorb for about 60 minutes. The stick was placed in blocking solution (TBS, 5% horse serum) for a minimum of 15 minutes.

II. Preparation of the Adsorbent Beads

To minimize the contribution of certain samples' affinity to bind to proteins denatured on solid surfaces (or solid surfaces directly) and to effect removal of contaminating human anti-GAG (soluble or in complexes), latex polystyrene particles were covalently coupled with recombinant HIV-1 p24 GAG protein. The recombinant antigen is made 100-200 micrograms/ml in PBS. The antigen solution was added to washed and pelleted latex particles. The solution was triturated and exposed for 20 seconds of an ultrasonic bath. The final concentration of beads was 0.5%. Solid carbodiimide is added to make a final concentration of about 5 milligrams per ml. The solution is rotated gently for one hour at room temperature and washed (with PBS) and pelleted (12,000×g) three minutes, room temperature 3 times. The final bead solution is made 0.01% to 0.5% (w/v) in blocking buffer. III. Sample Tray The first compartment contained 2.5 ml of blocking buffer containing about 0.1% recombinant antigen adsorbent beads described above. The second compartment contained 2.5 milliliters wash solution (TBS). The third compartment contained 2.5 milliliters of developing conjugate solution, polyclonal goat anti-HIV-1 GAG coupled to alkaline phosphatase diluted 1:500 in blocking solution. The fourth compartment contained 2.5 milliliters of wash solution (TBS). The fifth compartment contained 2.5 milliliters of presubstrate wash solution (pH 10 alkaline buffer).

IV. The Assay 100 microliters of patient sample (blood, serum, plasma) is added to a shallow well, containing twenty microliters of dissociation buffer (1M HCl-glycine buffer). The solution is then transferred into chamber #1. The solution was gently stirred with the test strip and allowed to incubate at 42° C. for about 20 minutes. Care was taken to ensure that the readable area was maximally exposed to the solvent phase. The strip was transferred to compartment #2 and washed for about 10 seconds. The strip was transferred to compartment #3 with about five seconds of gentle stirring. The strip was allowed to incubate for about 20 minutes at 42° C. The strip was transferred to compartment #4 and gently stirred for about 10 seconds. The strip was transferred to compartment #5 and washed for about 10 seconds. The strip was removed and tapped lightly to remove excess liquid. One drop (about 50 microliters) of substrate (5-bromo-4-chloro-3-indolyl phosphate, Sigma catalog #B-0766, in alkaline buffer, pH 10) was added to each readable area. After approximately 10 minutes, the color reaction of each readable area was recorded as positive (blue color) or negative (no color).

EXAMPLE 4

HIV-1 GAG Protein Antigen Test Format

I. The Dipstick

Test strip (dipstick) prototypes were constructed from injection molding of polystyrene or polystyrene treated to give a white opaque stick to have the shape of 5 wells in a row with the same spacing as that of a 96 well microtiter plate (see FIG. 1).

All proteins added at 50 microliters per well were in 0.1M sodium bicarbonate buffer pH 9.6.

Stick Well #1 [Top]—anti-human IgG (5 micrograms per well)
Stick Well #2 —anti-HIV-1 GAG protein (5 micrograms per well)
Stick Well #3 [Bottom]—negative control monoclonal (5 micrograms per well)

Sticks were placed in a humidified incubator/oven for 1 hour at 45° C. The sticks were removed, solutions were aspirated and 100 microliters of 5% non-fat milk/TBS were added to each well. Sticks were incubated for 60 minutes at 37° C. in a humidified incubator/oven and then solutions were aspirated. 100 microliters of a 10% sucrose/4% PVP (polyvinylpyrrolidone), 0.1% sodium azide solution was added to each well, incubated for 15 minutes at room temperature and then aspirated. After air drying for about 10 minutes, the sticks were then stored desiccated at 2°-8° C.

II. The Assay

Tube 1

Tube 1 was pre-coated with 3.0 ml of 50 micrograms/ml each of equine IgG, goat IgG, and non-reactive mouse IgG in TBS azide by incubation for 30 minutes in a 37° C. water bath followed by decanting of the coating solution. The tubes were allowed to dry in an inverted position and then used.

Tube 1 contained beads coated with either 1) goat immunoglobulin (IgG) or 2) bovine IgG or 3) horse IgG or 4) non-reactive mouse monoclonal antibody 0.01% v/v for each of the four types of coated beads (0.04% v/v total coated beads), 9% serum (3% horse, 3% bovine, 3% goat) in 0.05M Tris-HCl buffer pH 7.2 and 0.15M sodium chloride (TBS). The final volume was 1.5 ml.

150-300 microliters of patient whole blood or 50-150 microliters of fresh serum or plasma (preferably not frozen) was used.

The sample was allowed to incubate at room temperature with the beads/tube for 5 minutes before the dipstick was added.

The tube with dipstick was incubated at 37° C. in a water bath for 60 minutes.

The dipstick was removed, tapped gently on an absorbent pad, and then placed in Tube 2.

Tube 2

The tube contained TBS wash solution. The final volume was 5-40 ml depending on specific application.

The dipstick was swirled for 5-10 seconds, tapped gently on an absorbent pad, and then placed in Tube 3.

Tube 3

Tube 3 contained biotinylated rabbit anti-HIV-1 GAG protein and 5% horse serum in TBS. The final volume equaled 1.5 ml.

The dipstick was incubated for 60 minutes at 37° C. It was then gently tapped on absorbent pad and added to Tube #4.

Tube 4

Tube 4 contained a TBS wash. The final volume was 5–40 ml depending on the specific application.

The dipstick was swirled for 5–10 seconds, then gently tapped on an absorbent pad and added to Tube 5.

Tube 5

Tube 5 contained a 1.5 ml solution of strepavidin-horseradish peroxidase 5% horse serum and TBS. The dipstick was incubated for 30 minutes at 37° C. It was gently tapped on an absorbent pad and then added to Tube 6.

Tube 6

The tube contained a TBS wash. The final volume was 540–40 ml depending on the specific application.

The stick was swirled for 5–10 seconds, gently tapped on an absorbent pad and then added to Tube 7.

Tube 7

The tube contained a TBS wash. The final volume was 540–40 ml depending on the specific application. The stick was swirled for 5–10 seconds, gently tapped on an absorbent pad. The stick was then placed horizontally on a flat surface.

III. Color Development

One drop (50 microliters) of 3,3', 5,5'-Tetramethylbenzidine (TMB) substrate was added to each well. After 10 minutes, the reaction was stopped with a drop.(15–25 microliters) of 2N HCl. The wells were then read as either negative, weak, or positive according to the presence or absence of a yellow color.

IV. Results

The optical density is given in Table 1.

TABLE 1

|  | Serum | Serum + Antigen |
| --- | --- | --- |
| Negative Control MAb | 0.045 | 0.051 |
| Anti-GAG MAb | 0.065 | 0.142 |

EXAMPLE 5

HIV-1 Antibody Test Format

I. The Dipstick

Test strip (dipstick) prototypes were constructed from injection molding of polystyrene or polystyrene treated to give a white opaque stick to have the shape of 5 wells in a row with the same spacing as that of a 96 well microtiter plate (see FIG. 2).

All proteins added at 50 microliters per well were in TBS/0.1% sodium azide.

Stick Well #1 [Top]—positive control—anti-human IgG monoclonal antibody (5 micrograms per well)
Stick Well #2—HIV-1 recombinant ENV protein (0.5 micrograms per well)
Stick Well #3—negative control (no coat)
Stick Well #4 [Bottom]—HIV-1 recombinant GAG protein (0.5 micrograms per well Sticks were placed in a humidified incubator/oven for 1 hour at 45° C. The sticks were removed, solutions were aspirated and 100 microliters of 5% horse serum/TBS azide were added to each well. Sticks were incubated for 40 minutes at room temperature, then solutions were aspirated. 100 microliters of a 10% sucrose/4% PVP (polyvinylpyrrolidone), 0.1% sodium azide solution was added to each well, incubated for 15 minutes at room temperature and then aspirated. After air drying for about 10 minutes, the sticks were then stored desiccated at 2°–8° C.

II. The Assay

All steps of this procedure are carried out at room temperature unless otherwise noted.

Tube 1

Tube 1 was pre-coated by adding 3.0 ml. of 50 microgram/ml of each of bovine, horse and goat IgG in 0.05M Tris-HCl buffer pH 7.2 with 0.15M sodium chloride (TBS) and 0.1% sodium azide (azide). The solution is incubated for 30 minutes in a 37° C. water bath and then decanted. The tubes are used after drying in an inverted position on an absorbent pad. Tube 1 contained beads coated with either 1) goat immunoglobulin (IgG) or 2) bovine IgG or 3) horse IgG 0.01% v/v for each of the three types of coated beads (0.03% v/v total coated beads), 9% serum (3% horse, 3% bovine, 3% goat) in 0.05M Tris-HCl buffer pH 7.2, 0.15M sodium chloride (TBS), and 0.1% sodium azide. The final volume was 1.9 ml.

300 microliters of patient whole blood or 100–150 microliters of fresh serum or plasma (preferably not frozen) was used.

The sample was allowed to incubate for 5 minutes at room temperature with the beads/tube before the dipstick was added.

The tube with dipstick was incubated for 30 minutes at room temperature (22°–25° C.).

The dipstick was removed, tapped gently on an absorbent pad, and then placed in Tube 2.

Tube 2

The tube contained TBS wash solution with 0.1% sodium azide. The final volume was 5–40 ml depending on the specific application.

The dipstick was swirled for 5–10 seconds, tapped gently on an absorbent pad, and then placed in Tube 3.

Tube 3

Tube 3 contained goat anti-human IgG—alkaline phosphatase, 5% horse serum in TBS, and 0.1% sodium azide. The final volume equaled 2 ml.

The dipstick was incubated for 10 minutes at room temperature (22°–25° ). It was then gently tapped on an absorbent pad and added to Tube #4.

Tube 4

Tube 4 contained a TBS wash with 0.1% sodium azide. The final volume was 5–40 ml. depending on the specific application.

The dipstick was swirled for 5–10 seconds, then gently tapped on an absorbent pad and added to Tube 5.

Tube 5

Tube 5 contained a TBS wash with 0.1% sodium azide. The stick was swirled for 5–10 seconds and then gently tapped on an absorbent pad. The stick was then laid horizontally on a flat surface.

III. Color Development

One drop (50 microliters) of 5-bromo-4-choloro-3-indolyl phosphate (BCIP) substrate (0.1M glycine buffer, pH 10.4, 0.1% sodium azide) was added to each well. After 10 minutes, the reaction was stopped with a drop (15–25 microliters) of EDTA (25 mM). The wells were then read as either negative, weak, or positive according to the presence or absence of a blue color.

IV. Results:

TEST A

Using the HIV-1 recombinant ENV protein well as an indicator of an HIV-1 exposure, the subject invention's test results agreed with an FDA licensed anti-HIV ELISA test in 51 out of 53 double blind samples (Table 2). The two samples that tested differently, wherein the subject invention tested negative and the FDA licensed anti-HIV ELISA tested positive, were Western Blot indeterminate.

A second FDA licensed HIV-1 ELISA antibody test results differed from the first FDA licensed anti-HIV ELISA test in 14 out of 53 samples. In all 14 samples, the second FDA licensed HIV-1 ELISA test was positive and

TABLE 2

| Sample # | 1* | 2* | 3* | Difference 2vs3* | Difference 3vs1* | Comments |
|---|---|---|---|---|---|---|
| 1 | − | − | + | + | | |
| 2 | + | + | + | | | |
| 3 | + | + | + | | | |
| 4 | + | + | + | | | |
| 5 | − | − | − | | | |
| 6 | + | + | + | | | |
| 7 | − | − | + | + | | |
| 8 | + | + | + | | | |
| 9 | − | − | + | + | | |
| 10 | − | − | + | + | | |
| 11 | + | + | + | | | |
| 12 | + | + | + | | | |
| 13 | − | + | + | | + | Western Blot Indeterminate |
| 14 | + | + | + | | | |
| 15 | + | + | + | | | |
| 16 | − | − | + | + | | |
| 17 | + | + | + | | | |
| 18 | + | + | + | | | |
| 19 | + | + | + | | | |
| 20 | + | + | + | | | |
| 21 | − | − | + | + | | |
| 22 | + | + | + | | | |
| 23 | − | − | + | + | | |
| 24 | − | − | + | + | | |
| 25 | − | − | − | | | |
| 26 | − | − | − | | | |
| 27 | + | + | + | | | |
| 28 | − | − | + | + | | |
| 29 | + | + | + | | | |
| 30 | + | + | + | | | |
| 31 | − | − | − | | | |
| 32 | − | − | + | + | | |
| 33 | − | − | − | | | |
| 34 | − | − | − | | | |
| 35 | − | − | + | | | |
| 36 | − | − | + | | | |
| 37 | − | − | + | | | |
| 38 | + | + | + | | | |
| 39 | − | − | − | | | |
| 40 | + | + | + | | | |
| 41 | + | + | + | | | |
| 42 | − | − | + | + | | |
| 43 | − | + | + | | + | Western Blot Indeterminate |
| 44 | − | − | + | + | | |
| 45 | + | + | + | | | |
| 46 | + | + | + | | | |
| 47 | − | − | + | + | | |
| 48 | − | − | − | | | |
| 49 | − | − | − | | | |
| 50 | − | − | − | | | |
| 51 | + | + | + | | | |
| 52 | + | + | + | | | |
| 53 | − | − | + | + | | |

1* - Subject Invention Test
2* - First FDA Licensed anti-HIV ELISA Test
3* - Second FDA Licensed anti-HIV ELISA Test
2vs3* - results of First and Second FDA Licensed Tests Compared;
3vs1* results of Second FDA Licensed Test and Subject Invention Test Compared.

the first FDA licensed HIV-1 ELISA test as well as the subject invention's were negative.

These data suggest that there is agreement between the results of the subject inventions test and the first FDA licensed test, except in the case where the first FDA licensed test is positive and Western Blot results are indeterminate. The two samples that fall into this exception are tested negative with the subject invention test. In 14 out of 53 samples, the subject invention test and first FDA licensed test results were negative whereas the second FDA licensed test was positive. These data collectively suggest that the subject invention test has no false positives unlike the second FDA licensed test and, in addition, does not register a response when the Western Blot is indeterminate.

TEST B

Twenty double blind samples (serum or plasma) were utilized. Using the ENV wells of the subject invention as an indicator of an HIV-1 exposure, 14 samples were identified as positive and 6 as negative. These results agreed with the second FDA licensed HIV-1 ELISA test in all but two samples. Two samples were known to be false positives according to the second FDA licensed HIV-1 ELISA test (tested positive by the second FDA licensed HIV-1 ELISA test, negative by Western Blot). One of these two samples contained icteric blood and the other contained lipemic blood. These data suggest that the subject invention test had no false positives unlike the second FDA licensed HIV-1 ELISA test and could correctly identify that test's true positives. (See Table 3.)

TABLE 3

| SAMPLE # | 1* GAG | ENV | 2* |
|---|---|---|---|
| 1 | − | − | − |
| 2 | − | − | false positive |
| 3 | + | + | + |
| 4 | − | + | + |
| 5 | − | + | + |
| 6 | − | − | − |
| 7 | − | + | + |
| 8 | − | − | − |
| 9 | + | + | + |
| 10 | − | + | + |
| 11 | − | − | − |
| 12 | + | + | + |
| 13 | + | + | + |
| 14 | − | − | − |
| 15 | + | + | + |
| 16 | + | + | + |
| 17 | − | − | false positive |
| 18 | − | + | + |
| 19 | + | + | + |
| 20 | + | + | + |

1* - Subject Invention Test
2* - Second FDA Licensed anti-HIV ELISA Test

TEST C

Patient 1 was followed over the course of a two month period from Day 1 to Day 73. Eighteen different sample points were taken. On blood samples drawn on Day 1, Day 8 and Day 10, seven FDA licensed HIV-1 antibody tests all registered negative for the presence of HIV-1 antibody (Tests 1–7 in Table 4). The subject invention test is shown as Test 8 in Table 4. All observers (5) scored a negative for samples drawn on Day 1 and Day 8. However, all observers scored a positive reaction for the subject invention test for the Day 10 sample. All samples from Day 15 thereafter were positive with the subject invention test. On the Day 15 sample, Day 17 and Day 22 samples, only the seventh test picked up a positive response. On Day 24, the second and seventh samples now registered positive for HIV-1 antibody. From Day 29 on, all seven licensed tests detected the presence of HIV-1 antibody. The Western Blot test had been negative up to Day 15 and became GAG positive (ENV negative) from Day 17 to Day 24. Only at Day 29 when all the other licensed test kits were positive was the Western Blot positive for both ENV and GAG.

These results suggest the subject invention test is more sensitive than all seven commercially licensed HIV-1 antibody tests. Both the subject invention test and the seventh test appeared to be more sensitive than the Western Blot.

TEST D

A second patient was followed longitudinally beginning at Day 1 and ending Day 96. (See Table 5) The Western Blot had been equivocal (p53/55 ±, GAG negative, ENV negative) for the first nine samples and not until the tenth sample (Day 96) was the Western Blot positive. In addition, all seven licensed kits were negative for the first nine samples and all were positive by Day 96.

TABLE 4

DETECTION OF anti-HIV AND HIV ANTIGEN(S) IN LONGITUDINALLY COLLECTED SAMPLES FROM A PLASMA DONOR (Donor C)

Test Run Reference[1]

| DAY NO. | (1) | (2) | (3) | (4) | (5) | (6) | (7) | (8) | (9) | (10) | (11) | (12) |
|---|---|---|---|---|---|---|---|---|---|---|---|---|
| PANEL C | | | | | | | | | | | | |
| 1 | − | − | − | − | − | − | − | − | − | − | − | − |
| 8 | − | − | − | − | − | − | − | − | − | − | − | + |
| 10 | − | − | − | − | − | − | − | + | − | − | − | + |
| 15 | − | − | − | − | − | − | + | + | − | − | − | − |
| 17 | − | − | − | − | − | − | + | + | − | +/− | − | − |
| 22 | − | − | − | − | − | − | + | + | − | +/− | + | − |
| 24 | − | + | − | − | − | − | + | + | − | +/− | + | − |
| 29 | + | + | + | + | + | + | + | + | − | + | + | − |
| 31 | + | + | + | + | + | + | + | + | − | + | + | − |
| 36 | + | + | + | + | + | + | + | + | − | + | + | − |
| 43 | + | + | + | + | + | + | + | + | − | + | + | − |
| 45 | + | + | + | + | + | + | + | + | − | + | + | − |
| 57 | + | + | + | + | + | + | + | + | − | + | + | − |
| 59 | + | + | + | + | + | + | + | + | − | + | + | − |
| 64 | + | + | + | + | + | + | + | + | − | + | + | − |
| 66 | + | + | + | + | + | + | + | + | − | + | + | − |
| 71 | + | + | + | + | + | + | + | + | − | + | + | − |
| 73 | + | + | + | + | + | + | + | + | − | + | + | − |

[1](1) = anti-HIV ELISA
(2) = anti-HIV ELISA
(3) = anti-HIV ELISA
(4) = anti-HIV ELISA
(5) = anti-HIV ELISA
(6) = anti-HIV ELISA
(7) = anti-HIV ELISA
(8) = subject invention
(9) = anti-H9 ELISA
(10) = anti-HIV WESTERN BLOT
(11) = anti-HIV IFA
(12) = HIV Antigen(s) ELISA ELISA (control) results were generated using commercially available FDA licensed anti-HIV screening tests. The IFA, WB and HIV Antigen data were generated with unlicensed products (research use only) whose test characteristics have not yet been fully determined.
All samples were assayed under code by individuals who routinely use these test procedures.

TABLE 5

DETECTION OF anti-HIV AND HIV ANTIGEN(S) IN LONGITUDINALLY COLLECTED SAMPLES FROM FIVE PLASMAPHERESIS DONORS Test Run Reference[1]

| DAY NO. | (1) | (2) | (3) | (4) | (5) | (6) | (7) | (8) | (9) | (10) | (11) | (12) |
|---|---|---|---|---|---|---|---|---|---|---|---|---|
| PANEL D | | | | | | | | | | | | |
| 1 | − | − | − | − | − | − | − | − | − | +/− | − | − |
| 8 | − | − | − | − | − | − | − | − | − | +/− | − | − |
| 22 | − | − | − | − | − | − | − | − | − | +/− | − | − |
| 36 | − | − | − | − | − | − | − | + | − | +/− | − | − |
| 43 | − | − | − | − | − | − | − | + | − | +/− | − | − |
| 50 | − | − | − | − | − | − | − | − | − | +/− | − | − |
| 64 | − | − | − | − | − | − | − | − | − | +/− | − | − |
| 85 | − | − | − | − | − | − | − | − | − | +/− | − | + |
| 92 | − | − | − | − | − | − | − | − | − | +/− | − | + |
| 96 | + | + | + | + | + | + | + | + | − | + | + | − |

[1](1) = anti-HIV ELISA
(2) = anti-HIV ELISA
(3) = anti-HIV ELISA
(4) = anti-HIV ELISA
(5) = anti-HIV ELISA
(6) = anti-HIV ELISA
(7) = anti-HIV ELISA
(8) = subject invention
(9) = anti-H9 ELISA
(10) = anti-HIV WESTERN BLOT
(11) = anti-HIV IFA
(12) = HIV Antigen(s) ELISA Although there were discrepancies among the five independent observers, weak reactions had been observed in the subject invention test as early as the first sample (Day 1). Four out of five observers observed weak to positive reactions on samples drawn on Day 36 and Day 43. Three out of five observers noticed weak to positive reaction on ENV for the Day 43 sample. The ENV reaction was not observed by any readers on the Day 50 sample.

These data suggest that for this patient, the subject invention test is more sensitive than the seven licensed test kits and the Western Blot. Over a 4 month period, there was a waxing and waning of a response to both GAG and ENV until Day 96 when there was a clear response to ENV and GAG.

TEST E

Twenty-five patient samples, all positive for the presence of antibody to HTLV-1, were used for this test. Five of these samples were reportedly reactive in a licensed HIV-1 antibody test. The subject invention test recorded a positive reaction for both GAG and ENV in the noted HIV-1 antibody positive serum. However, three sera were noted with reactivity to ENV, where one sample (#R) was clearly ENV positive according to the subject invention test and shown to be Western Blot positive for ENV. These data would suggest that a tube was possibly mislabeled as HIV-1 antibody negative. The other two positive samples were both weakly reactive, suggesting that these patients may have a weak response to HIV-1 ENV. With respect to those samples that were ENV negative by the test of the subject invention, 1 out of 17 sera were positive for GAG according to the test of the subject invention. These data suggest that the GAG antigen used in the subject invention test is highly specific for HIV-1 with minimal cross reactivity to HTLV-1. However, one should be cautious in interpreting GAG reactivity along (no ENV reactivity) in the subject invention test. It would be advised that GAG reactivity alone would be a suspicious exposure to a human retrovirus but could only be confirmed as HIV-1 infection at a later date if ENV reactivity appears.

TEST F

The plasma of twelve HIV-1 infected patients were tested for HIV-1 antigen in a commercially-available antigen GAG antigen HIV-I ELISA test system. Three out of twelve patients showed significant levels of HIV-1 antigen (GAG antigen) in their blood.

In the subject invention test measuring antibodies against GAG and ENV, all twelve patients were strongly reactive in the ENV well. However, only eight patients were weakly to strongly reactive in the GAG well. These eight patients were shown to be antigen negative by the commercially-available antigen test. Three negative subject invention GAG patients were all reactive in the commercially-available antigen test. One subject invention GAG negative sample was negative on the commercially-available antigen test.

From this study, it would appear that the loss of subject invention test GAG reactivity in HIV-1 infected individuals correlates with the rise of antigenemia.

TEST G

Ten normal volunteers provided blood drawn in tubes containing the anti-coagulant EDTA. 300 microliters of whole blood was added to the subject invention tube #1 and the test processed. The identity of all 10 volunteers remained blinded. In ten out of ten cases there were no positives in the negative control, GAG or ENV wells for any of the bloods. In the case of normal whole blood spiked with patient serum, the subject invention test result was not inhibited by the presence of whole blood.

TEST H—URINE SAMPLES

Ten concentrated urine samples (100X) were used. All ten samples were coded. The test procedure was different from the format described previously for blood. The sample was diluted 1/20 and allowed to incubate with the beads and dipstick for a total of two hours at room temperature. The stick was washed in tube #2 and then allowed to react in tube #3 for a total of 30 minutes at room temperature. The rest of the reaction was carried out as described in the original format. Seven urines were reactive for the ENV. Of those seven, two were reactive also for GAG. Three urines were unreactive for ENV and GAG. All ten urines were reactive with the positive control (antihuman immunoglobulin). The seven ENV positives identified by the subject invention test were all Western Blot positive HIV-1 infected individuals. The three ENV, GAG subject invention negative urines were from normal volunteers (non HIV-1 infected individuals).

The results are shown in Table 6. These data show that the subject invention antibody test for blood can be designed to detect HIV-1 antibodies in concentrated urines.

TEST I

Fifty unconcentrated urine samples were tested with a recombinant HIV-1 envelope antigen (the carboxyterminus of gp120 and an immunoreactive part of ENV). Twenty-seven samples were from asymptomatic HIV-1 seropositive individuals. Three samples were from AIDS/ARC patients. Twenty samples were from HIV-1 seronegative individuals. Undiluted samples were incubated with the beads and dipstick for a total of two hours at room temperature. The stick was washed in tube #2 and then allowed to react in tube #3 for a total of 30 minutes at room temperature. The rest of the reaction was carried out as previously described. All 30 urine samples from HIV-1 seropositive individuals were positive for HIV-1 recombinant envelope. All 20 urines from HIV-1 seronegative were negative for HIV-1 recombinant envelope. All 50 samples were reactive with the positive control (anti-human immunoglobulin). These data suggest that the subject invention antibody test for blood can be designed to detect HIV-1 antibodies in unconcentrated urines.

TABLE 6

| SAMPLE # | 1* GAG | ENV | 2* ELISA | Western Blot gp160 | gp120 | p66 | p55 | p51 | gp41 | p31 | p24 | p19 | RIPA |
|---|---|---|---|---|---|---|---|---|---|---|---|---|---|
| 1 | + | + | + | √ | √ | √ | √ | √ | √ | √ | √ | − | |
| 2 | + | + | + | √ | √ | √ | √ | √ | √ | √ | √ | √ | gp160, p66, gp44, p24 |
| 3 | − | + | + | √ | √ | − | − | − | √ | √ | − | − | gp160, gp41 |
| 4 | − | + | + | √ | √ | − | − | − | − | √ | − | − | |
| 5 | − | + | + | √ | √ | √ | − | − | √ | √ | √ | − | gp160, p66, p24 |
| 6 | − | + | + | √ | √ | √ | √ | √ | √ | √ | √ | √ | |

TABLE 6-continued

| SAMPLE # | 1*<br>GAG | ENV | 2*<br>ELISA | Western Blot gp160 | gp120 | p66 | p55 | p51 | gp41 | p31 | p24 | p19 | RIPA |
|---|---|---|---|---|---|---|---|---|---|---|---|---|---|
| 7 | − | + | + | √ | √ | √ | √ | √ | √ | √ | − | − | gp160, p51, p24 |
| 8 | − | − | − | | | | | | | | | | |
| 9 | − | − | − | | | | | | | | | | |
| 10 | − | − | − | | | | | | | | | | |
| 11 | | | | | | | | | | | | | |

1* - Subject Invention Test
2* - Commercial anti-HIV ELISA Test

SUMMARY

From two longitudinal studies, the subject invention antibody test appears to be more sensitive than all seven commercially licensed FDA HIV-1 antibody tests and the Western Blot.

From the Test A, the subject invention test appears to be more sensitive for ENV than the Western Blot.

The subject invention test appears to have no false positives as judged in Test A nor is it reactive in the case of Western Blot indeterminates.

The subject invention HIV-1 antibody test seems to be highly specific for HIV-1 exposure with minimal cross reactivity in patients infected solely with HTLV-1.

The subject invention test may be used to follow HIV-1 infected individuals that develop antigenemia by observing the levels of anti-GAG protein reactivity.

The subject invention test appears to work on whole blood. This means a physician can draw blood in an anti-coagulant tube, and directly add the whole blood to the subject invention test kit and know the results within 1 hour at room temperature.

The subject invention test kit also detects HIV-1 antibodies in urine. The fact that human immunoglobulin could be found in all ten urine samples (both normal and HIV-1 infected individuals) suggests that the coated beads and coated tubes now used in the subject invention test kit for blood will be required for urine.

Selecting the correct ENV protein in this equilibrium assay allows the subject invention to pick up HIV-1 antibodies in unconcentrated urine. Urine is a preferred choice of sample material for two reasons: 1) unlike blood, urine contains none to little HIV-1 infectious material; and 2) no venipuncture is required, minimizing infection due to accidental needle sticks.

EXAMPLE 6

Simultaneous HIV-1 GAG antigen and HIV-1 ENV antibody test format

I. The Dipstick

Test strip (dipstick) prototypes were constructed from injection molding of polystyrene or polystyrene treated to give a white opaque stick to have the shape of 5 wells in a row with the same spacing as that of a 96 well microtiter plate (see FIG. 2).

All proteins added at 50 microliters per well.

Stick Well #1 [Top]—positive control—anti-human IgG monoclonal antibody (5 micrograms per well)

Stick Well #2—anti-HIV-1 GAG protein monoclonal antibody (5 micrograms per well)

Stick Well #3—negative control monoclonal antibody (5 micrograms per well)

Stick Well #4—HIV-1 ENV antigen (0.5 micrograms per well)

Stick Well #5 [Bottom]—negative control (no coat)

The stick was placed horizontally solution side up into a humidified 45° oven and reagents were allowed to adsorb for about 60 minutes. The stick was placed in blocking solution (TBS 5% horse serum for negative control and ENV; TBS 5% nonfat milk for antibodies) for 60 minutes at 37° C.

II. Assay

Tube 1

Tube 1 was coated before use with 3.0 ml of 50 micrograms/ml in TBS/azide of each of equine IgG, bovine IgG and goat IgG by incubation for 30 minutes in a 37° C. water bath followed by decanting of the coating solution. The tubes were allowed to dry in an inverted position and then used.

Tube 1 contained beads coated with either 1) goat immunoglobulin (IgG) or 2) bovine IgG or 3) horse IgG or 4) non-reactive mouse monoclonal antibody 0.01% v/v for each of the four types of coated beads (0.04% v/v total coated beads), 9% serum (3% horse, 3% bovine, 3% goat) in 0.05M Tris-HCl buffer pH 7.2 and 0.15M sodium chloride (TBS). The final volume was 2.5 ml.

300 microliters of patient whole blood or 100–150 microliters of fresh serum or plasma (preferably not frozen) was used.

The sample was allowed to incubate at room temperature with the beads/tube for 5 minutes before the dipstick was added.

The tube with dipstick was incubated at 37° C. in a water bath for 60 minutes.

The dipstick was removed, tapped gently on an absorbent pad, and then placed in Tube 2.

Tube 2

The tube contained TBS wash solution. The final volume was 5–40 ml depending on the specific application.

The dipstick was swirled for 5–10 seconds, tapped gently on an absorbent pad, and then placed in Tube 3.

Tube 3

Tube 3 contained both biotinylated rabbit anti-HIV-1 GAG protein and biotinylated rabbit anti-human in 5% horse serum and TBS. The final volume equaled 2.5 ml. The dipstick was incubated for 60 minutes at 37° C. It was then gently tapped on absorbent pad and added to Tube #4.

Tube 4

Tube 4 contained a TBS wash. The final volume was 5–40 ml depending on the specific application.

The dipstick was swirled for 5–10 seconds, then gently tapped on an absorbent pad and added to Tube 5.

Tube 5

Tube 5 contained a solution of strepavidin-horseradish peroxidase in 5% horse serum and TBS. The dipstick was incubated for 30 minutes at 37° C. It was gently tapped on an absorbent pad and then added to Tube 6.

Tube 6

The tube contained a TBS wash. The final volume was 5–40 ml depending on the specific application.

The stick was swirled for 5-10 seconds, gently tapped on an absorbent pad and then added to tube 7.

Tube 7

The tube contained a TBS wash. The final volume was 5-40 ml depending on the specific application.

The stick was swirled for 5-10 seconds, gently tapped on an absorbent pad. The stick was then placed horizontally on a flat surface.

II. Color Development

One drop (50 microliters) of 3,3', 5,5'-Tetramethylbenzidine (TMB) substrate was added to each well.

After 10 minutes, the reaction was stopped with a drop (15-25 microliters) of 2N HCl. The wells were then read as either negative, weak, or positive according to the presence or absence of a yellow color.

IV. Results

Table 7 shows the optical density for the following serum samples:
1. normal human;
2. normal human plus GAG antigen;
3. HIV-1 seropositive, GAG antigen negative; and
4. HIV-1 seropositive, GAG antigen negative plus GAG antigen.

TABLE 7

Simultaneous Testing for HIV-1 Antibody and Antigen

| Well Contents | NHS | Serum Sample NHS + AG | Patient | Patient + Ag |
|---|---|---|---|---|
| Negative Control | 0.01 | 0.01 | 0.01 | 0.01 |
| HIV1 ENV | 0.01 | 0.02 | 0.22 | 0.19 |
| Negative MAb Control | 0.06 | 0.07 | 0.06 | 0.06 |
| Anti-GAG MAb | 0.06 | 0.15 | 0.06 | 0.19 |
| Anti-Human IgG | 1.02 | 0.90 | 0.85 | 0.98 |

NHS = Normal Human Serum
Patient = HIV-1 seropositive, GAG antigen negative
Ag = GAG Antigen, 300 pg/ml
MAb = Monoclonal Antibody
HIV-1 GAG Antigen free serum was spiked with 300 pg per ml. of GAG protein. Serum was then added to the E1 format and tested. The results show that the E1 dipstick can simultaneously detect the presence of antibody in the same serum sample. In addition, the stick can be used either for antibody capture or antigen capture.

What is claimed is:

1. A kit for detecting the presence of a target human antibody to human immunodeficiency virus (HIV) in a urine sample comprising
   a) a treatment buffer comprising non-immune sera and about 0.01% to 0.5% (w/v) of a plurality of solid phase particles from about 0.5 microns to about 10 microns in diameter, the plurality of solid phase particles comprising equal volumes of three particle types, each particle type coated with goat, bovine, or horse immunoglobulin antibodies, the non-immune sera comprising 3% bovine serum, 3% goat serum, and 3% horse serum;
   b) a labelled reagent comprising an enzyme label conjugated to an anti-human immunoglobulin antibody;
   c) a substrate specific for the enzyme label; and
   d) a reagent HIV antigen.

2. A buffer comprising non-immune sera and about 0.01% to 0.5% (w/v) of a plurality of solid phase particles from about 0.5 microns to about 10 microns in diameter, the plurality of solid phase particles comprising equal volumes of three particle types, each particle type coated with goat, bovine, or horse immunoglobulin antibodies, the non-immune sera comprising 3% bovine serum, 3% goat serum, and 3% horse serum.

3. A method for detecting the presence of a target human antibody to HIV in a urine sample, said method comprising:
   a) adding a treatment buffer to the sample, which buffer comprises non-immune sera and 0.01% to 0.5% (w/v) of a plurality of solid phase particles from about 0.5 microns to about 10 microns in diameter, the plurality of solid phase particles comprising equal volumes of three particle types, each particle type coated with goat, bovine, or horse immunoglobulin antibodies, the non-immune sera comprising 3% bovine serum, 3% goat serum, and 3% horse serum; and
   b) contacting the sample with a reagent HIV antigen to form an antigen-antibody complex containing the target human antibody and the HIV antigen;
   c) contacting the antigen-antibody complex with an enzyme labeled anti-human immunoglobulin antibody that specifically binds to the target human antibody; and
   d) detecting the presence of the bound label as an indication of the presence of any target antibody in the urine sample.

4. The method of claim 3 wherein the HIV antigen is gp160, gp120 or gp41 glycoprotein, or p24 protein.

5. A method of detecting an HIV antibody in a saliva, urine, or whole or fractionated blood sample from a human subject, said method comprising:
   a) contacting the sample with a recombinant HIV glycoprotein under conditions such that the glycoprotein specifically binds to any HIV antibody present in the sample to form a complex;
   b) contacting the complex with an enzyme labeled anti-human immunoglobulin antibody which specifically binds and labels the complex to form a labeled complex; and
   c) detecting the presence of enzyme labeled complex and thereby the presence of any HIV antibody in the sample wherein a treatment buffer is added to the sample before, or simultaneous with, contacting the sample with the glycoprotein, said treatment buffer comprising non-immune sera and about 0.01% to 0.5% (w/v) of a plurality of solid phase particles from about 0.5 microns to about 10 microns in diameter, the plurality of solid phase particles comprising equal volumes of three particle types, each particle type coated with goat, bovine, or horse immunoglobulin antibodies, the non-immune sent comprising 3% bovine serum, 3% goat serum, and 3% horse serum.

6. A method for detecting in a sample from a human subject the presence of a target human antibody to HIV which specifically binds an HIV vital antigen, said method comprising:
   a) adding to the sample a treatment buffer comprising non-immune sera and about 0.01% to 0.5% (w/v) of a plurality of solid phase particles from about 0.5 microns to about 10 microns in diameter, the plurality of solid phase particles comprising equal volumes of three particle types, each particle type coated with goat, bovine, or horse immunoglobulin antibodies, the non-immune sent comprising 3% bovine serum, 3% goat serum, and 3% horse serum;
   b) using a test strip comprising
      i) a solid support;
      ii) said HIV viral antigen bound to a first discrete area on the solid support;

iii) a non-target human antibody bound to a second discrete area on the solid support as a positive control; and iv) a negative control which will not specifically bind target human antibody or antihuman antibody bound to a third discrete area on the solid support;

c) contacting the treated sample with the test strip under conditions such that the HIV viral antigen bound to the test strip specifically binds with any target human antibody present in the treated sample;

d) washing the test strip to remove unbound treated sample;

e) contacting the resulting test strip with enzyme labeled antihuman antibodies which specifically bind to any target human antibodies bound to, or on, the test strip;

f) detecting the presence of enzyme labeled antibodies and thereby the presence of target human antibodies in the sample; and g) verifying the correctness of the detection by determining that the positive control is enzyme labeled and the negative control is not enzyme labeled.

7. The method of claim 6 wherein the sample comprises urine, saliva, or whole or fractionated blood.

8. A method for detecting in a sample from a human subject the presence of a target human antibody to HIV which specifically bins an HIV viral antigen, said method comprising:

a) adding to the sample a treatment buffer comprising non-immune sera and about 0.01% to 0.5 (w/v) of a plurality of solid phase particles from about 0.5 microns to about 10 microns in diameter, the plurality of solid phase particles comprising equal volumes of three particle types each particle type coated with goat, bovine, or horse immunoglobulin antibodies, the non-immune sen comprising 3% bovine serum, 3% goat serum, and 3% horse serum;

b) using a test strip comprising:
  i) wells used as a solid support;
  ii) said HIV viral antigen bound to discrete areas on the solid support;

c) contacting the treated sample with the test strip under conditions such that the HIV viral antigen bound to the test strip specifically binds with any target human antibody present in the treated sample;

d) washing the test strip to remove unbound treated sample;

e) contacting the resulting test strip with enzyme labeled antihuman antibodies which specifically bind to any target human antibodies bound to, or on, the test strip; and f) detecting the presence of any bound enzyme labeled antibodies using a substrate for the enzyme and thereby the presence of the target human antibodies in the treated sample.

9. The method of claim 8, wherein the HIV viral antigen is gp160, gp120 or gp41 glycoprotein, or p24 protein.

10. The method of claim 8 wherein the HIV viral antigen is recombinant gp 160.

* * * * *